United States Patent
Masai et al.

(10) Patent No.: US 6,716,609 B2
(45) Date of Patent: Apr. 6, 2004

(54) POLYPEPTIDES HAVING α-HYDROXY-γ-CARBOXYMUCONIC ACID-ε-SEMIALDEHYDE DEHYDROGENASE ACTIVITY

(75) Inventors: Eiji Masai, Nagaoka (JP); Masao Fukuda, Nagaoka (JP); Yoshihiro Katayama, Nerima-ku (JP); Seiji Nishikawa, Satte (JP); Yasushi Hotta, Satte (JP)

(73) Assignees: Cosmo Research Institute, Tokyo (JP); Cosmo Oil Co., Ltd., Tokyo (JP)

( * ) Notice: Subject to any disclaimer, the term of this patent is extended or adjusted under 35 U.S.C. 154(b) by 0 days.

(21) Appl. No.: 09/983,306

(22) Filed: Oct. 24, 2001

(65) Prior Publication Data

US 2002/0098562 A1 Jul. 25, 2002

Related U.S. Application Data

(62) Division of application No. 09/720,817, filed as application No. PCT/JP99/03410 on Jun. 25, 1999, now Pat. No. 6,340,579.

(30) Foreign Application Priority Data

Jul. 17, 1998 (JP) .......................................... 10/203200

(51) Int. Cl.[7] .............................. C12P 17/06; C12N 9/02
(52) U.S. Cl. ..................... 435/125; 435/189; 435/252.3
(58) Field of Search .............................. 435/189, 252.3, 435/125

(56) References Cited

PUBLICATIONS

Y. Noda, et al., "Molecular Cloning of the Protocatechuate 4,5–Dioxygenase Genes of *Pseudomonas paucimobilis*", *Journal of Bacteriology*, May 1990, vol. 172, No. 5, pp. 2704–2709.

K. Yrjala, et al., "Novel Organization of Catechol Meta–Pathway Genes in *Sphingomonas sp.* HV3 pSKY4 Plasmid", *FEMS Microbiology Letters*, 1997, vol. 154, pp. 403–408.

U. Riegert, et al., "Distal Cleavage of 3–Chlorocatechol by an Extradiol Dioxygenase to 3–Chloro–2–Hydroxymuconic Semialdehyde", *Journal of Bacteriology*, Jun. 1998, vol. 180, No. 11, pp. 2849–2853.

M. F. Reid, et al., Critical Reviews in Microbiology, vol. 20, No. 1, pp. 13–56, XP–002110760, "Molecular Characterization of Microbial Alcohol Dehydrogenases", 1994.

K. Maruyama, et al., Journal of Biochemistry, vol. 83, No. 4, pp. 1125–1134, XP–002219348, "Purification and Properties of Alpha Hydroxy Gamma Carboxymaconic Epsilon-semialdehyde Dehydrogenase", 1978.

*Primary Examiner*—Charles L. Patterson, Jr.
(74) *Attorney, Agent, or Firm*—Oblon, Spivak, McClelland, Maier & Neustadt, P.C.

(57) ABSTRACT

α-Hydroxy-γ-carboxymuconic acid-ε-semialdehyde dehydrogenase, a gene encoding the enzyme, a recombinant vector containing the gene and a transformant carrying the gene, and processes for producing the enzyme and 2-pyronedicarboxylic acid by using the transformant.

Use of the transformant can produce α-hydroxy-γ-carboxymuconic acid-ε-semialdehyde dehydrogenase in a large amount, thereby permitting industrial production of 2-pyrone-4,6-dicarboxylic acid.

13 Claims, 1 Drawing Sheet

POLYPEPTIDES HAVING α-HYDROXY-γ-CARBOXYMUCONIC ACID-ε-SEMIALDEHYDE DEHYDROGENASE ACTIVITY

This application is a Divisional of Ser. No. 09/720,817, filed Jan. 12, 2001 (now U.S. Pat. No. 6,340,579), which was filed as International Application No. PCT/JP99/03410 on Jun. 25, 1999.

TECHNICAL FIELD

This invention relates to α-hydroxy-γ-carboxymuconic acid-ε-semialdehyde dehydrogenase as an enzyme which converts α-hydroxy-γ-carboxymuconic acid-ε-semialdehyde into 2-pyrone-4,6-dicarboxylic acid, a gene encoding this enzyme, a recombinant vector containing this enzyme, and a transformant carrying this gene; and also to a process for producing the enzyme and 2-pyrone-4,6-dicarboxylic acid by using the enzyme.

BACKGROUND ART

α-Hydroxy-γ-carboxymuconic acid-ε-semialdehyde dehydrogenase is an enzyme which converts α-hydroxy-γ-carboxymuconic acid-ε-semialdehyde into 2-pyrone-4,6-dicarboxylic acid, and plays an important role in the production of 2-pyrone-4,6-dicarboxylic acid useful as raw materials for polymers. Therefore, it is extremely important for the production of 2-pyrone-4,6-dicarboxylic acid to determine the gene of α-hydroxy-γ-carboxymuconic acid-ε-semialdehyde dehydrogenase and further to mass-produce α-hydroxy-γ-carboxymuconic acid-ε-semialdehyde dehydrogenase encoded by the gene.

On the other hand, remarkable developments have been achieved in recent years on recombinant DNA technology as mass production technology for proteins such as enzymes, resulting in successful mass production of numerous enzymes, physiologically-active proteins and the like by using recombinant DNA technology. Concerning α-hydroxy-γ-carboxymuconic acid-ε-semialdehyde dehydrogenase, however, the gene which encodes the enzyme has not been isolated yet.

An object of the present invention is to provide a technique for mass-producing 2-pyrone-4,6-dicarboxylic acid by isolating the gene of α-hydroxy-γ-carboxymuconic acid-ε-semialdehyde dehydrogenase and then enhancing the activity of α-hydroxy-γ-carboxymuconic acid-ε-semialdehyde dehydrogenase encoded by the gene.

DISCLOSURE OF THE INVENTION

The present inventors have proceeded with extensive research on microbiological production of 2-pyrone-4,6-dicarboxylic acid. As a result, the present inventors have succeeded in isolating, from a microorganism which contains α-hydroxy-γ-carboxymuconic acid-ε-semialdehyde dehydrogenase that converts α-hydroxy-γ-carboxymuconic acid-ε-semi-aldehyde into 2-pyrone-4,6-dicarboxylic acid, the gene of α-hydroxy-γ-carboxymuconic acid-ε-semialdehyde dehydrogenase by using recombinant DNA technology and further in determining its base sequence. In addition, the present inventors have also found a process for forming a recombinant vector of the gene and a transformant carrying the gene and then producing the enzyme and 2-pyrone-4,6-dicarboxylic acid, leading to the completion of the present invention.

The present invention, therefore, provides α-hydroxy-γ-carboxymuconic acid-ε-semialdehyde dehydrogenase having an amino acid sequence represented by SEQ ID NO: 1 or SEQ ID NO: 3 or an amino acid sequence with one or more amino acids deleted, substituted or added in the first-mentioned amino acid sequence, a gene encoding the enzyme, a recombinant vector containing the gene, and a transformant carrying the gene.

The present invention also provides a process for producing 2-pyrone-4,6-dicarboxylic acid, which comprises cultivating the transformant in the presence of α-hydroxy-γ-carboxymuconic acid-ε-semialdehyde.

Further, the present invention also provides a process for producing the enzyme, which comprises cultivating the transformant and collecting α-hydroxy-γ-carboxymuconic acid-ε-semialdehyde dehydrogenase from the resulting culture.

Use of the transformant according to the present invention permits production of α-hydroxy-γ-carboxymuconic acid-ε-semialdehyde dehydrogenase in a large amount, thereby making it possible to perform industrial production of 2-pyrone-4,6-dicarboxylic acid.

BEST MODES FOR CARRYING OUT THE INVENTION

Although no particular limitation is imposed on an isolation method of the gene in the present invention, a host-vector system of a microorganism can be used as an example. The gene can be produced, for example, by using recombinant DNA technology as will be described next. Described specifically, using as a DNA donor a microorganism having ability to convert α-hydroxy-γ-carboxymuconic acid-ε-semialdehyde into 2-pyrone-4,6-dicarboxylic acid, genome DNA is first extracted from the microorganism and then spliced with a restriction endonuclease into a DNA fragment. On the other hand, using a restriction endonuclease, ends between which the genome DNA fragment can be inserted are formed in a vector DNA such as a phage or plasmid. These genome DNA fragment and opened vector DNA are caused to join together with a DNA ligase, whereby a recombinant vector is obtained. The recombinant vector is transferred into a host cell, and a transformant carrying the target recombinant vector is selected. The target recombinant vector is isolated from the recombinant cell, whereby the gene according to the present invention is produced.

No particular limitation is imposed on the DNA donor in the present invention insofar as it is a microorganism having ability to convert α-hydroxy-γ-carboxymuconic acid-ε-semialdehyde into 2-pyrone-4,6-dicarboxylic acid. Illustrative are Sphingomonas microorganisms, with Sphingomonas sp. CR-0300100 and its mutant, Sphingomonas sp. CR-0310201 (FERM BP-6748), being particularly preferred.

The extraction of the genome DNA from the microorganism may be performed preferably by collecting cultivated cells of the microorganism, lysing the cells, for example, with protease K, and then conducting procedures—such as deproteinization treatment by extraction with phenol, protease treatment, ribonuclease treatment, precipitation of the genome DNA with an alcohol and centrifugation—in combination as needed.

The splicing of the separated genome DNA into fragments can be conducted, for example, by digestion of the genome DNA with a restriction endonuclease.

As the vector, it is preferred to use one constructed from a pharge or plasmid, which can autonomously replicate in a host microorganism, with a view to providing a recombinant vector. Preferred examples of the plasmid can include pBR322, pUC18, pUC19, pUC118, pUC119, bluescript, pKK223-3, pACYC177, RSF1010 and pKT230, which use *Escherichia coli* as a host. These vectors are used after forming ends, between which a DNA fragment can be inserted, with a restriction endonuclease, for example, and optionally subjecting the ends to dephosphoryzation.

Joining between the genome DNA fragment and the vector DNA fragment may preferably be conducted using a known DNA ligase, for example, T4 DNA ligase or the like.

As the host microorganism into which the thus-obtained recombinant vector is to be transferred, any microorganism can be used insofar as it permits stable and autonomous replication of the recombinant vector and stable expression of characters of the foreign gene. For example, *Escherichia coli* or *Pseudomonas putida* is usable.

As a method for transferring the recombinant vector into the host microorganism, any method can be used including, for example, conjugation, electroporation, the competent cell technique, microinjection and the particle gun technique.

Selection of the transformant can be conducted using, as an index, a selected marker of the used vector, for example, drug resistance which is acquired by the recombination of DNA by the transformant. Selection of a transformant, which contains the target recombinant vector, out of these transformants may preferably be conducted, for example, by colony hybridization which makes use of a partial DNA fragment of the gene as a probe. Usable examples of a label for this probe can include radioisotopes, digoxigenin, enzymes and the like.

To extraction the recombinant vector from the transformant so selected, extraction can be performed by a method known per se in the art. For example, alkali lysis [Cold Spring Harbor Laboratory Press, Molecular Cloning, Second Edition (1989)] can be used.

The extracted recombinant vector can be recombined further by using recombinant DNA technology. To cut out the gene of the present invention from the recombinant vector so obtained, a restriction endonuclease or the like can be used.

The base sequence of the gene of the present invention obtained as described above can be determined, for example, by reading it in accordance with the dideoxy method. The base sequences of genes which encode α-hydroxy-γ-carboxymuconic acid-ε-semialdehyde dehydrogenase are shown under SEQ ID NO:2 and SEQ ID NO:4; the amino acid sequences of the above-described enzyme, which are estimated from the base sequences, are indicated under SEQ ID NO: 1 and SEQ ID NO: 3; and the base sequence and estimated amino acid sequence of a DNA fragment isolated in an Example, which will be described subsequently herein, are presented under SEQ ID NO: 5.

SEQ ID NO: 1 is a partial amino acid sequence of SEQ ID NO: 3. Enzymes according to the present invention have similar enzymatic activity no matter they have the amino acid sequence of SEQ ID NO: 3 or the amino acid sequence of SEQ ID NO: 1. It is to be noted that enzymes—which have amino acid sequences similar to the amino acid sequence of SEQ ID NO: 1 or SEQ ID NO: 3 except that one or more amino acids have been deleted, substituted or added—and genes encoding polypeptides of these enzymes are embraced by the present invention insofar as the polypeptides have the activity of α-hydroxy-γ-carboxymuconic acid-ε-semialdehyde dehydrogenase.

Likewise, SEQ ID NO: 2 is a partial base sequence of SEQ ID NO. 4. It is also to be noted that base sequences similar to the base sequence described under SEQ ID NO: 2 or SEQ ID NO: 4 except that one or more bases have been deleted, substituted or added are encompassed by the present invention.

To express the gene of the present invention and to produce α-hydroxy-γ-carboxymuconic acid-ε-semialdehyde dehydrogenase, it is only necessary to cultivate a transformant carrying the gene of the present invention, for example, the above-described transformant, a transformant with a recombinant vector formed by inserting the gene of the present invention in an expression vector having a strong promoter, a transformant with a recombinant vector formed by inserting the gene of the present invention in a vector having a high copy number in a cell, or a transformant with a recombinant vector formed by inserting the gene of the present invention in an expression vector having a strong promoter and a high copy number and then to collect the dehydrogenase from the culture. In this case, the cultivation is conducted depending on the properties of the used transformant, for example, at pH 5–8 and 20–37° C. on a culture medium which contains a carbon source, a nitrogen source, vitamins, etc.

When the transformant according to the present application is cultivated, α-hydroxy-γ-carboxymuconic acid-ε-semialdehyde dehydrogenase is expressed with high yield. Accordingly, cultivation of the transformant in the presence of α-hydroxy-γ-carboxymuconic acid-ε-semialdehyde makes it possible to efficiently produce 2-pyrone-4,6-dicarboxylic acid. Here, α-hydroxy-γ-carboxymuconic acid-ε-semialdehyde as a substrate for the enzyme may be added into the culture medium but, when the transformant also produces, for example, an enzyme which converts 3,4-dihydroxybenzoic acid into α-hydroxy-γ-carboxymuconic acid-ε-semialdehyde, addition of 3,4-dihydroxybenzoic acid into the culture medium and subsequent cultivation result in the production of α-hydroxy-γ-carboxymuconic acid-ε-semialdehyde and then in the production of 2-pyrone-4,6-dicarboxylic acid. Conditions for the production of 2-pyrone-4,6-dicarboxylic acid should be set depending on properties of the used transformant.

Collection of 2-pyrone-3,4-dicarboxylic acid from the culture is conducted, for example, by extraction with an organic solvent.

EXAMPLES

The present invention will next be described more specifically by the following Examples. It should, however, be borne in mind that the present invention is by no means limited by the following Examples.

Referential Example 1

(1) A culture medium of the composition shown in Table 1, which contained 0.2% of syringic acid, was filled in 10-mL aliquots in 21-mm test tubes, and soil samples (0.5 g) were placed in the respective test tubes, followed by cultivation at 30° C. for 3 days.

TABLE 1

| Composition of culture medium | | Composition of sss | |
|---|---|---|---|
| $KH_2PO_4$ | 0.85 g | MgO | 10.75 g |
| $Na_2HPO_4$ | 4.9 g | $CaCO_3$ | 2.0 g |
| $(NH_4)_2SO_4$ | 0.5 g | $FeSO_4.7H_2O$ | 4.5 g |
| $MgSO_4.7H_2O$ | 0.1 g | $ZnSO_4.7H_2O$ | 1.44 g |
| $FeSO_4.7H_2O$ | 0.005 g | $MnSO_4.4H_2O$ | 1.12 g |
| sss (stock salt sol) | 0.1 mL/L | $CuSO_4.5H_2O$ | 0.25 g |
| | | $CoSO_4.7H_2O$ | 0.28 g |
| | | $H_3BO_3$ | 0.06 g |
| | | conc. HCl | 51.3 mL/L |

(2) The test tubes were next left standstill for about 5 minutes, and slightly turbid supernatants were subcultivated in aliquots of 0.1 mL to fresh test tubes of the same composition, followed by cultivation at 30° C. for 3 days.

(3) The above procedures were repeated 1 to 2 times. Final supernatants were appropriately diluted in sterilized distilled water, were spread over an agar medium which had the composition presented in Table 1 and contained 0.2% of syringic acid, and were then cultivated at 30° C. for 3 days, whereby colonies were formed.

(4) The colonies were inoculated with toothpicks onto an agar medium which had the composition presented in Table 1 and contained 0.2% of vanillic acid, and grown cell strains were obtained.

(5) The cell strains grown on vanillic acid were inoculated again onto the culture medium (10 mL) which had the composition presented in Table 1 and contained 0.2% of syringic acid, and were cultivated at 30° C. for 3 days. The cultures were appropriately diluted in sterilized distilled water, spread over LB agar medium and cultivated 30° C. for 1 day, whereby colonies were formed.

(6) To two types of agar media which had the composition shown in Table 1 and contained 0.2% of vanillic acid and 0.2% of syringic acid, respectively, the colonies so formed were inoculated with toothpicks separately depending on their types. Grown cell strains were obtained.

(7) A cell strain capable of growing on both of the two agar media, which contained vanillic acid and syringic acid, respectively, was obtained. The cell strain was designated "CR-0300100", and its taxonominal characteristics were investigated. The following results were obtained.

| | |
|---|---|
| a. Morphological characteristics | |
| Cell size and shape | 0.5 × 1.1 to 1.3 μm, rod |
| Spores | None |
| Flagella | Polar flagellation |
| Mobility | + |
| b. Growth on agar medium | |
| On the medium in Table 1 | Glossy, yellow, circular colony |
| c. Physiological properties | |
| Gram strain | − |
| Reduction of nitrate salts | − |
| Gelatin liquefaction | + (weak) |
| O-F test | O: +, F: − |
| Viable range | pH 5.0 to 7.5, 10° C. to 40° C. |
| Assimilation of carbon sources | |
| Glucose | + |
| Sucrose | + |
| Lactose | − |
| Glycerol | − |
| Starch | − |
| Vanillin | + |
| Vanillic acid | + |
| Syringic aldehyde | + |
| Syringic acid | + |
| Cytochrome oxidase | + |
| Catalase | + |
| d. Chemotaxonomical properties | |
| GC content in DNA (mole %) | 68 |
| Quinone type | Q-10 |
| Pigment | + (hydrophobic yellow pigment) |
| Cell wall lipid | Sphingolipid |
| e. Other characteristics | |
| 3,4-Dihydroxybenzoic acid oxidase | Metacleavage |

From the above-described properties, CR-0300100 strain was identified as being of the genus Sphingomonas.

Referential Example 2

(1) Using 100 mL of LB medium (tryptone 10 g, yeast extract 5 g, sodium chloride 5 g, glucose 1 g/L), Sphingomonas sp. CR-0300100 obtained in Referential Example 1 was cultivated under shaking at 30° C. for 24 hours. After cells were collected by centrifugation, whole DNAs were extracted by the Marmur's method (Marmur, J.: J. Mol. Biol., 3, 208–218, 1961) and then purified by a method known per se in the art.

(2) The whole DNAs of Sphingomonas sp. CR-0300100, which had been obtained in step (1), were fully degraded with restriction endonucleases XhoI and SphI and then mixed with a vector plasmid pUC19 which had been fully digested with restriction endonucleases SalI and SphI. The resulting mixture was treated with T4 DNA ligase such that a hybrid plasmid was formed.

(3) The hybrid plasmid obtained in step (2) was transferred into *E. coli* HB101. The strain so transformed was spread on LB medium, which contained 100 mg/L of ampicillin, such that 200 to 300 colonies would appear per plate, and was cultivated at 37° C. for 18 hours.

(4) Colonies obtained in the above step were subcultivated at an inoculum size of 96 colonies per plate onto LB medium which contained 100 mg/L of ampicillin, and were used as master plates. By those procedures, colonies of 2,000 strains were obtained in total. Those colonies were each separately inoculated into a 96-well microplate, each of the wells of which contained 0.2 mL of LB medium containing 100 mg/L of ampicillin. Shaking cultivation was then conducted at 37° C. on a microplate shaker.

(5) After cultivated for 18 hours, lisozyme was added to each well such that its final concentration reached 50 μg/ml, followed by incubation at 37° C. for 2 hours. Next, a 20 mM solution of 3,4-dihydroxybenzoic acid was added in aliquots of 2 μL to the individual wells, followed by incubation 30° C. for 5 minutes.

(6) When 2 M sodium hydroxide was added in aliquots of 10 μL to the individual wells, development of a yellow color was observed on one of the 2,000 strains.

(7) A plasmid was extracted from the strain which developed the yellow color, and its cleavage pattern was investigated with respect to several restriction endonucleases. This plasmid was named "pPX150".

Referential Example 3

(1) pPX150 was cut by restriction endonuclease ApaI, whereby self-ligated plasmid pPX151 was prepared. *E. coli*

HB101 transformed with that plasmid and *E. coli* HB101 transformed with pPX150 were cultivated for 18 hours on 10-mL portions of LB medium which contained 100 mg/L of ampicillin, and cells were collected. Those cells were suspended in 1 mL of 50 mM phosphate buffer and were then disrupted by an ultrasonic disrupter. The disrupted mixture was centrifuged under 5,000 g for 20 minutes. A 20-µL aliquot of the resultant supernatant was added to 1 mL of phosphate buffer which contained 0.2 mM of 3,4-dihydroxybenzoic acid. When 0.1 mL of 2 M sodium hydroxide was added subsequent to incubation for 5 minutes at 30° C., development of a yellow color was observed on *E. coli* HB101 transformed with pPX150 but development of a yellow color was not observed on *E. coli* HB101 transformed with pPX151.

(2) Plasmid pUC4K (product of Pharmacia Biotech AB) was digested with restriction endonuclease EcoRI, subjected to blunting with a blunting kit (product of TAKARA SHUZO CO., LTD.), and then separated by electrophoresis on 1% agarose gel.

(3) A 1.3 kbp fragment was cut out from the gel and then subjected three times to extraction with phenol. The resulting DNA was purified by precipitation in ethanol.

(4) pPX151 was cleaved with restriction endonuclease ApaI and then subjected to blunting with the blunting kit (product of TAKARA SHUZO CO., LTD.). The blunted mixture and the DNA obtained above in step (3) were combined together and then subjected to a ligating reaction with a ligation kit (product of TAKARA SHUZO CO., LTD.). The transformed DNA was transferred into *E. coli* HB101. As transformed *E. coli* HB101, a strain resistant to kanamycin and ampicillin was selected, and pPX152 was obtained as a plasmid carried by the strain.

Referential Example 4

(1) Plasmid pPX152 obtained in the preceding experiment was digested with restriction endonuclease XbaI and then separated by electrophoresis on 1% agarose, and a 2.3 kbp fragment was cut out. Then, DNA was extracted by the freezing and thawing method, fully extracted with phenol, and purified by precipitation in ethanol.

(2) Sphingomonas sp. CR-0300100 was cultivated at 28° C. for 23 hours in 500 mL of LB liquid medium (with 25 mg/L of nalidixic acid contained therein), and the culture was then cooled for 15 minutes in ice.

(3) Cells were collected at 4° C. for 10 minutes under 10,000 rpm. Subsequent to gentle washing with 500 mL of distilled water of 0° C., the cells were collected again by centrifugation. After the cells were gently washed with 250 mL of distilled water of 0° C., the cells were collected by centrifugation. Further, the cells were gently washed with 125 mL of distilled water of 0° C. and then collected by centrifugation.

(4) The cells were suspended in distilled water which contained 10% of glycerol, and were held at 0° C.

(5) Distilled water (4 µL), which contained about 0.05 µg of DNA obtained above in step (1), was placed in a 0.2 cm-cuvette, followed by the addition of 40 µL of the competent cells obtained above in step (4). The resulting mixture was subjected to electroporation under the conditions of 25 µF, 2,500 V, 12 msec.

(6) The cells treated as described above were wholly inoculated to 10 mL of LB liquid medium, followed by cultivation at 30° C. for 6 hours. After the cultivation, cells were collected by centrifugation, spread on LB plate with 25 mg/L of kanamycin contained therein, and then cultivated at 30° C. for 48 hours.

(7) Under the above conditions, a very strong kanamycin resistant strain was obtained. This strain was named "Sphingomonas sp. CR-0310201".

(8) Sphingomonas sp. CR-0310201 and CR-0300100 were cultivated on 10-ml portions of LB medium for 24 hours, and cells were collected. Those cells were suspended in 1 mL of 50 mM phosphate buffer and were then disrupted by an ultrasonic disrupter. The disrupted mixture was centrifuged under 5,000 g for 20 minutes. A 100-µL aliquot of the resultant supernatant was added to 1 mL of phosphate buffer which contained 0.2 mM of 3,4-dihydroxybenzoic acid. When 0.1 mL of 2M sodium hydroxide was added subsequent to incubation for 5 minutes at 30° C., development of a yellow color was observed on CR-0300100 but development of a yellow color was not observed on CR-0310201. CR-0310201 showed exactly the same taxonominal characteristics as CR-0300100 except that CR-0310201 did not have the above-mentioned properties, resistance to kanamycin and assimilability of vanillic acid. This cell strain has been deposited as FERM BP-6748 under the Budapest Treaty with National Institute of Bioscience and Human-Technology, Agency of Industrial Science and Technology, Ministry of International Trade and Industry (address: 1-3, Higashi 1-chome, Tsukuba-shi, Ibaraki-ken305-8566, Japan) (date of original deposit: Feb. 4, 1998).

Example 1

(Analysis of the amino acid sequence of α-hydroxy-γ-carboxymuconic acid-ε-semialdehyde dehydrogenase)

Sphingomonas sp. CR-0310201 was cultivated at 30° C. for 24 hours under aerobic conditions on LB liquid medium, and cells were collected by centrifugation. With respect to the cell strain so collected, cell disruption treatment was conducted at 150 W for 10 minutes by an ultrasonic disrupter, followed by centrifugation under 100,000 g for 30 minutes.

The supernatant was subjected to ammonium sulfate fractionation. Fractions corresponding to ammonium sulfate concentrations of from 30 to 70 wt. % were collected, and enzymes were purified by weak-anion-exchange chromatography [product of Perseptive Biosystems, Inc., PI (polyethylimine) column], strong-anion-exchange chromatography [product of Perseptive Biosystems, Inc., HQ (quaternary polyethylimine)], hydrophobic chromatography (product of Pharmacia AB, "Phenyl Sepharose CL-4B") and adsorption chromatography (hydroxyapatite). Fractions having the activity of α-hydroxy-γ-carboxymuconic acid-ε-semialdehyde dehydrogenase were collected.

The purified product, which had been subjected to the purification through the columns, was confirmed to appear as a single band as a result of SDS-PAGE, and was hence ascertained to have been a single enzyme.

Partial amino acid sequences of the thus-isolated α-hydroxy-γ-carboxymuconic acid-ε-semialdehyde dehydro-genase were analyzed by an amino acid sequencer (manufactured by Applied Biosystems, Inc.). The thus-determined partial amino acid sequences of the enzyme are shown under SEQ ID NO: 7 and SEQ ID NO: 8.

Incidentally, the activity of α-hydroxy-γ-carboxymuconic acid-ε-semialdehyde dehydrogenase was determined as will be described hereinafter.

(1) On the medium presented in Table 1 and contained 2 g/L of parahydroxybenzoic acid, Pseudomonas testosteroni JMC5832 was cultivated in a dark place under shaking at 30° C. for 24 hours.

(2) Cells were collected by centrifugation, suspended in a potassium phosphate buffer of pH 7.5, subjected to cell disruption treatment at 150 W for 10 minutes by an ultrasonic disrupter, and then centrifuged under 10,000 g for 30 minutes.

(3) To the supernatant obtained as described above, an equal amount of ethanol was added, followed by centrifugation under 10,000 g for 10 minutes. Ethanol was added to the thus-obtained supernatant such that the concentration of ethanol reached 70% (v/v), followed by further centrifugation under 10,000 g for 10 minutes.

(4) A precipitate, which was obtained in the above step, was dissolved in a 50 mM potassium phosphate buffer (pH 7.5) which contained 10% of ethanol. Using a 200 mM potassium phosphate buffer (pH 7.5) containing 10% of ethanol, a metacleavage enzyme fraction of 3,4-dihydroxybenzoic acid was obtained by a DEAE-cellulose column.

(5) 50 μL of the metacleavage enzyme solution of 3,4-dihydroxybenzoic acid, which had been obtained as described above, were added to 0.9 mL of a 50 mM Tris-HCl buffer (pH 8.1) which contained 0.2 mM of 3,4-dihydroxybenzoic acid. The resultant mixture was incubated at 37° C. while monitoring the absorbance at 410 nm by a spectrophotometer (manufactured by SHIMADZU CORP.; "UV-2100"). When the absorbance became constant, 50 μL of an α-hydroxy-γ-carboxymuconic acid-ε-semialdehyde dehydrogenase solution (1 mg in terms of protein weight) were added. After confirming that the absorbance remained unchanged by this procedure, 20 μL of NADP (100 mM solution) were added, and a decrease in absorbance at 410 nm was monitored for 100 seconds. From the NADP-dependent decrease in the amount of α-hydroxy-γ-carboxymuconic acid-ε-semialdehyde, the activity of α-hydroxy-γ-carboxymuconic acid-ε-semialdehyde dehydrogenase was determined.

Example 2

Cloning of the gene encoding α-hydroxy-γ-carboxymuconic acid-ε-semialdehyde dehydrogenase (1) Preparation of a Gene Library Sphingomonas sp. CR-0310201 was inoculated to LB medium (tryptone: 10 g/L, yeast extract: 5 g/L, NaCl: 5 g/L, pH 7.0) which contained 5 g/L of glucose and then cultivated overnight at 28° C., whereby a preculture was prepared. The preculture was inoculated to a similar culture medium as that mentioned above, which had been newly provided in a flask, and was again cultivated overnight at 28° C. Cells were collected by centrifugation of the culture.

After the cells were suspended in TE (10 mM Tris-HCl, 1 mM EDTA, pH 8.0), the resulting suspension was treated at 37° C. for 1 hour with a final concentration of 0.5% SDS and a final concentration of 100 μg/mL protease K. With the suspension so treated, ⅙ volume of 5 M sodium chloride was mixed. Then, ​1/10 volumes of 10% CTAB (hexadecyltrimethylammonium bromide) and 0.7 M sodium chloride were added, and the resulting mixture was allowed to stand at 65° C. for 10 minutes. The mixture was extracted with an equiamount of chloroform-isoamyl alcohol, and the resulting water layer was extracted with an equiamount of phenol-chloroform. Genome DNA which was contained in the water layer was obtained by ethanol precipitation and, subsequent to drying under reduced pressure, TE was added to dissolve the same.

The genome DNA was partially digested with restriction endonuclease EcoRI (product of TAKARA SHUZO CO., LTD.), followed by electrophoresis on 1% agarose (product of WAKO PURE CHEMICAL INDUSTRIES, LTD., "Agarose 1600"). TAE [Cold Spring Harbor Laboratory Press, Molecular Cloning, Second Edition (1989)] was used as a buffer. Subsequent to the electrophoresis, the agarose gel was immersed for 15 minutes in 1 μg/mL ethidium bromide and washed with water, and then, fluorescence from DNA fragments was confirmed by UV irradiation. As size markers, EcoRI and HindIII digestion products (products of TAKARA SHUZO CO., LTD.) of λphage DNA were subjected to electrophoresis at the same time, and from migrated distance of the DNA fragments, the molecular weights of digestion products of the genome DNA were determined.

Agarose gel containing EcoRI partial digestion products of the genome DNA, said partial digestion products being of 1 to 3 kbp, was cut out, and by the ultracentrifugation method making use of cesium chloride, purification of DNA fragments was conducted.

Plasmid vector pUC19 was completely digested with restriction endonuclease EcoRI (product of TAKARA SHUZO CO., LTD.). Alkaline phosphates (Bacterial Alkaline Phosphatase) (product of TAKARA SHUZO CO., LTD.) was added to the reaction mixture, and end-dephosphoryzation of a plasmid vector digested by the restriction endonuclease was conducted.

To the reaction mixture, ​1/10 volume of 3 M sodium phosphate (pH 5.2). and 2 volumes of ethanol were added. The resulting mixture was chilled at −80° C. for 2 hours and then centrifuged under 9,000 g for 10 minutes, whereby pellets of a vector DNA were obtained. 70% Ethanol was added twice in an amount as needed to rinse the wall of a centrifuge tube. After the rinsings were simply removed, the vector DNA was dried under reduced pressure. The dried vector DNA was dissolved in TE.

The above-described 1–3 kbp DNA fragments of Sphingomonas sp. CR-0310201 and the vector DNA were ligated together by using T4 ligase (product of TAKARA SHUZO CO., LTD.).

Competent cells of E. coli HB101 were prepared using 100 mM of calcium chloride, and were then transformed with the T4 ligase reaction mixture. The E. coli cells were spread on LB plate medium (which had been prepared by adding 15 g/L of agar to LB) which had been added with ampicillin such that its final concentration had reached 100 μg/mL, followed by overnight cultivation at 37° C. Formed colonies were collected as a gene library of Sphingomonas sp. CR-0310201 as obtained by using E. coli HB101 as a host.

(2) Preparation of a gene probe encoding α-hydroxy-γ-carboxymuconic acid-ε-semialdehyde dehydrogenase Sphingomonas sp. CR-0310201 was inoculated to a culture medium (polypeptone: 5 g/L, yeast extract: 0.5 g/L, meat extract:5 g/L, sodium chloride: 2 g/L, pH 7.0) placed in a test tube and was then cultivated overnight at 28° C., whereby a preculture was prepared. The preculture was inoculated to a similar culture medium as that mentioned above, which had been newly provided in a flask, and was again cultivated overnight at 28° C. Cells were collected by centrifugation of the culture.

After the cells were suspended in TE (10 mM Tris-HCl, 1 mM EDTA, pH 8.0), the resulting suspension was treated at 37° C. for 1 hour with a final concentration of 0.5% SDS and a final concentration of 100 μg/mL protease K. With the suspension so treated, ⅙ volume of 5 M sodium chloride was mixed. Then, ​1/10 volumes of 10% CTAB (hexadecyltrimethylammonium bromide) and 0.7 M sodium chloride were added, and the resulting mixture was allowed to stand at 65° C. for 10 minutes. The mixture was extracted with an equiamount of chloroform-isoamyl alcohol, and the resulting water layer was extracted with an equiamount of phenol-chloroform. Genome DNA which was contained in the water layer was obtained by ethanol precipitation and, subsequent to drying under reduced pressure, TE was added to dissolve the same.

Using partial amino acid sequences of the gene encoding α-hydroxy-γ-carboxymuconic acid-ε-semialdehyde dehydrogenase, said partial amino acid sequences being shown under SEQ ID NO: 7 and SEQ ID NO: 8, respectively, partial base sequences of the gene of α-hydroxy-γ-carboxymuconic acid-ε-semialdehyde dehydrogenase, said gene encoding these amino acid sequences, were inversely translated. From those findings, with a view to partially amplifying the gene by PCR, a synthetic nucleotide having base sequences shown under SEQ ID NO: 9 and SEQ ID NO: 10, respectively, was prepared by chemical synthesis, and was obtained as paired PCR primers. Using the genome DNA of Sphingomonas sp. CR-0310201 as DNA template, the partial DNA fragments of the gene of α-hydroxy-γ-carboxymuconic acid-ε-semialdehyde dehydrogenase were amplified by PCR making use of the primers.

Incidentally, this PCR was conducted as will be described next. Firstly, a reaction mixture containing 10 mM Tris-HCl (pH 8.3), 50 mM of potassium chloride, 1.5 mM of magnesium chloride, 0.001% (W/V) gelatin, 2 μM of dNTP mixed solution, 40 ng/μL of the genome DNA and 1 μM of the PCT primers was prepared. After the reaction mixture was heat-treated at 92° C. for 5 minutes, heat-resistant DNA polymerase (product of TAKARA SHUZO CO., LTD., "TaKaRa Taq") was added such that its concentration reached 0.05 U/μL, and the resultant mixture was left over at 40° C. for 6 minutes. After a chain reaction, which consisted of a thermal denaturation reaction at 94° C. for 30 seconds, an annealing reaction at 40° C. for 2 minutes, and an extending reaction at 72° C. for 30 seconds, was repeated 40 times, a reaction was conducted at 72° C. for 5 minutes.

Plasmid pPCCH1 with the amplified DNA fragment of about 600 bp ligated to plasmid vector pUC 19 was prepared. Using pPCCH1 as a DNA template, partial DNA fragments of the gene of α-hydroxy-γ-carboxymuconic acid-ε-semialdehyde dehydrogenase were amplified by PCR making use of the same PCR primers as those described above. In the second PCR, a chain reaction which consisted of a thermal denaturation reaction at 94° C. for 30 seconds, an annealing reaction at 40° C. for 2 minutes and an extending reaction at 72° C. for 30 seconds was repeated 40 times, and a reaction was then conducted at 72° C. for 5 minutes. The thus-obtained amplification product was subjected to electrophoresis, and an amplified DNA the molecular weight of which had increased as a result of insertion of digoxigenin-labeled nucleic acid was separated and cut out and was collected as an α-hydroxy-γcarboxymuconic acid-ε-semialdehyde dehydrogenase gene probe.

(3) Provision of a plasmid containing the gene of α-hydroxy-γ-carboxymuconic acid-ε-semialdehyde dehydrogenase About 2,000 strains of E. coli HB101 making up the library of Sphingomonas sp. CR-0310201, said library having been obtained above in step (1), were each separately inoculated with toothpicks onto a culture medium, which contained 100 g/mL of ampicillin, at an inoculum size of about 200 cells per 9-cm Petri dish. After static incubation at 37° C. for 6 hours, colonies were replicated onto nylon membranes, and colonies hybridizable with the probe obtained above in step (2) were selected using a DIG detection kit (product of Boehringer Mannheim Corporation) The selected E. coli strains carried plasmid pCHMS01.

Figure 1:
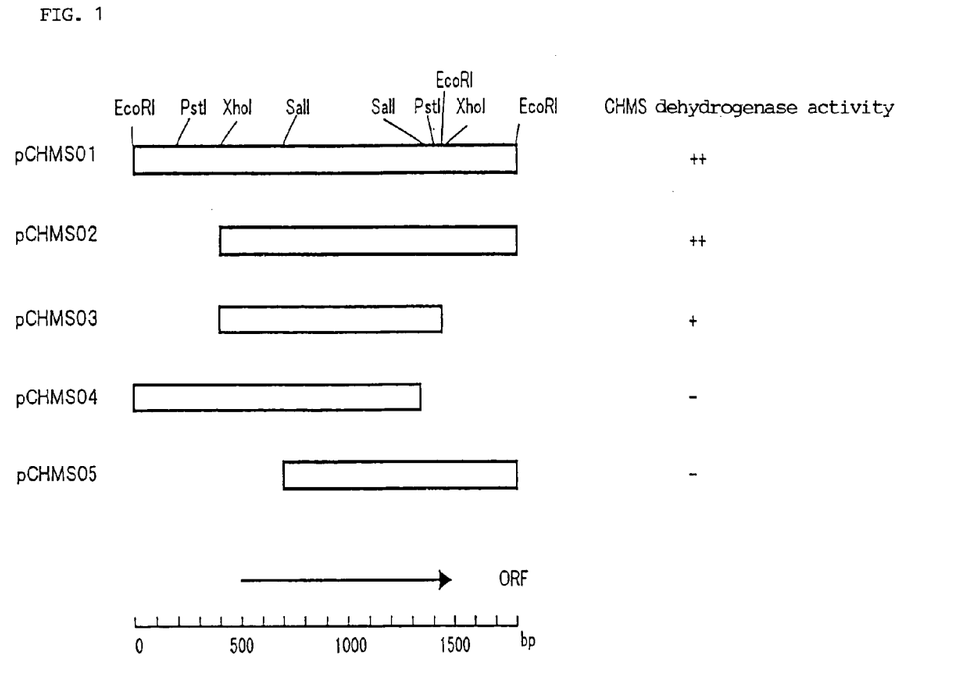
FIG. 1 is a diagram showing a restriction map of insert DNA fragments in plasmids, which contain the gene of α-hydroxy-γ-carboxymuconic acid-ε-semialdehyde dehydrogenase derived from Sphingomonas sp., and indicating existence or non-existence of activity of α-hydroxy-γ-carboxymuconic acid-ε-semialdehyde dehydrogenase.

(4) Measurement of α-hydroxy-γ-carboxymuconic acid-ε-semialdehyde dehydrogenase activity of the transformant E. coli strains—which carried plasmid pCHMS01 and plasmids prepared from pCHMS01 by using several restriction endonucleases, respectively—measured for α-hydroxy-γ-carboxymuconic acid-ε-semialdehyde dehydrogenase activity (FIG. 1). As a result, it has been confirmed that the gene of α-hydroxy-γ-carboxymuconic acid-ε-semialdehyde dehydrogenase is efficiently expressed on pCHMS01, pCHMS02 and pCHMS03.

Measurement of the α-hydroxy-γ-carboxymuconic acid-ε-semialdehyde dehydrogenase activity which each of the above-described transformants possessed was conducted as will be described next. To 50 mL of LB liquid medium added with ampicillin and IPTG at final concentrations of 100 μg/mL and 1 mM, respectively, E. coli JM109 which carried pCHMS01, pCHMS02, pCHMS03 or pCHMS04 was cultivated under shaking for 24 hours in 100 ml of LB medium containing 100 μg/mL of ampicillin. After cells were collected by centrifugation, the cells were washed twice with 50 mM Tris-HCl buffer (pH 7.5) and were then suspended in 5 mL of 50 mM Tris-HCl buffer (pH 7.5). Cell disruption treatment was conducted at 150 W for 10 minutes by an ultrasonic disrupter, whereby a cell-free extract was obtained. Using that cell-free extract as an enzyme solution, measurement of α-hydroxy-γ-carboxymuconic acid-ε-semialdehyde dehydrogenase activity was conducted as in Example 1. The reaction mixture was analyzed by HPLC ("BONDASPHEARE C 18 column", mobile phase: 2% acetic acid, 20% methanol, 78% distilled water), and formation of 2-pyrone-4,6-dicarboxylic acid was confirmed.

(5) Analysis of the base sequence of the gene of α-hydroxy-γ-carboxymuconic acid-ε-semialdehyde dehydrogenase Next, an analysis of the base sequence of the inserted DNA fragment of about 1.4 kbp was conducted using the recombinant plasmid pCHMS02. In this analysis of the base sequence, a sequencing reaction was carried out by the M13 dideoxy method [Sanger, F., et al., Proc. Natl. Acad. Sci., 74, 5463–5467 (1977) ] making use of a T7 sequencing kit (product of Pharmacia Biotech AB), and an automated laser fluorescence sequencer (manufactured by Pharmacia Biotech AB) was used. As a result of the analysis of the base sequence, only one open reading frame of 945 bp was found on the DNA fragment.

The base sequence of the gene encoding α-hydroxy-γ-carboxymuconic acid-ε-semialdehyde dehydrogenase, said gene having been obtained as described above, was analyzed. The base sequence and the coded amino acid sequence are shown under SEQ ID NO: 5.

Capability of Exploitation in Industry

The present invention is extremely useful for the production, especially mass-production of 2-pyrone-4,6-dicarboxylic acid which is used as raw materials for polymers.

What is claimed is:

1. An isolated polypeptide which has an α-hydroxy-γ-carboxymuconic acid-ε-semialdehyde dehydrogenase activity comprising:

the amino acid sequence of SEQ ID NO: 1 or 3, a fragment of the amino acid sequence of SEQ ID NO: 1 or 3 which has an α-hydroxy-γ-carboxymuconic acid-ε-semialdehyde dehydrogenase activity, or a modified amino acid sequence comprising SEQ ID NO: 1 or 3 or a fragment of SEQ ID NO: 1 or 3 which has an α-hydroxy-γ-carboxymuconic acid-ε-semialdehyde dehydrogenase activity, except for one deletion, insertion or substitution of an amino acid residue of SEQ ID NO: 1 or 3.

2. The polypeptide of claim 1, which comprises the amino acid sequence of SEQ ID NO:1 or SEQ ID NO: 3.

3. The polypeptide of claim 1, which comprises a fragment of SEQ ID NO: 1 or SEQ ID NO: 3, which has an α-hydroxy-γ-carboxymuconic acid-ε-semialdehyde dehydrogenase activity.

4. The isolated polypeptide of claim 1 that is a modified polypeptide comprising SEQ ID NO: 1 or 3, except for one deletion, insertion or substitution of an amino acid residue.

5. The isolated polypeptide of claim 1 that is a modified polypeptide comprising a fragment of SEQ ID NO: 1 or 3, which has an α-hydroxy-γ-carboxymuconic acid-ε-semialdehyde dehydrogenase activity, except for one deletion, insertion or substitution of an amino acid residue.

6. An isolated polypeptide comprising the amino acid sequence of SEQ ID NO: 7 or 8, wherein said polypeptide has an α-hydroxy-γ-carboxymuconic acid-ε-semialdehyde dehydrogenase activity.

7. The polypeptide of claim 1, which is present in a host cell.

8. A cell-free extract comprising the polypeptide of claim 1.

9. A composition comprising the polypeptide of claim 1.

10. A method for producing 2-pyrone-4,6-dicarboxylic acid comprising:

contacting α-hydroxy-γ-carboxymuconic acid-ε-semialdehyde with the polypeptide of claim 1 having an α-hydroxy-γ-carboxymuconic acid-ε-semialdehyde dehydrogenase activity for a time and under conditions suitable for producing 2-pyrone-4,6-dicarboxylic acid and collecting the 2-pyrone-4,6-dicarboxylic acid.

11. The method of claim 10, wherein said polypeptide having an α-hydroxy-γ-carboxymuconic acid-ε-semialdehyde dehydrogenase activity is present in a host cell.

12. The method of claim 10, wherein said collecting comprises extraction of 2-pyrone-4,6-dicarboxylic acid with an organic solvent.

13. A raw material or polymer comprising the 2-pyrone-4,6-dicarboxylic acid produced by the method of claim 10.

* * * * *

SEQUENCE LISTING

<160> NUMBER OF SEQ ID NOS: 10

<210> SEQ ID NO 1
<211> LENGTH: 280
<212> TYPE: PRT
<213> ORGANISM: Sphingomonas sp. CR-0310201
<300> PUBLICATION INFORMATION:

<400> SEQUENCE: 1

Met Arg Ile Ala Leu Ala Gly Ala Gly Ala Phe Gly Glu Lys His Leu
 1               5                  10                  15

Asp Gly Leu Lys Asn Ile Asp Gly Val Glu Ile Val Ser Ile Ile Ser
            20                  25                  30

Arg Lys Ala Glu Gln Ala Ala Glu Val Ala Ala Lys Tyr Gly Ala Lys
        35                  40                  45

His Ser Gly Thr Asp Leu Ser Glu Ala Leu Ala Arg Asp Asp Val Asp
    50                  55                  60

Ala Val Ile Leu Cys Thr Pro Thr Gln Met His Ala Glu Gln Ala Ile
65                  70                  75                  80

Ala Cys Met Asn Ala Gly Lys His Val Gln Val Glu Ile Pro Leu Ala
                85                  90                  95

Asp Ser Trp Ala Asp Ala Glu Ala Val Met Lys Lys Ser Gln Glu Thr
            100                 105                 110

Gly Leu Val Cys Met Val Gly His Thr Arg Arg Phe Asn Pro Ser His
        115                 120                 125

Gln Tyr Ile His Asn Lys Ile Val Ala Gly Glu Leu Ala Ile Gln Gln
    130                 135                 140

Met Asp Val Gln Thr Tyr Phe Phe Arg Arg Lys Asn Met Asn Ala Lys
145                 150                 155                 160

Gly Glu Pro Arg Ser Trp Thr Asp His Leu Leu Trp His His Ala Ala
                165                 170                 175

His Thr Val Asp Leu Phe Ala Tyr Gln Ala Gly Lys Ile Val Gln Ala
            180                 185                 190

Asn Ala Val Gln Gly Pro Ile His Pro Glu Leu Gly Ile Ala Met Asp
        195                 200                 205

Met Ser Ile Gln Leu Lys Ser Glu Thr Gly Ala Ile Cys Thr Leu Ser
210                 215                 220

Leu Ser Phe Asn Asn Asp Gly Pro Leu Gly Thr Phe Phe Arg Tyr Ile
225                 230                 235                 240

Cys Asp Asn Gly Thr Trp Ile Ala Arg Tyr Asp Asp Leu Val Thr Gly
                245                 250                 255

Lys Glu Glu Pro Val Asp Val Ser Lys Val Asp Val Ser Met Asn Gly
            260                 265                 270

Ile Glu Leu Gln Asp Arg Glu Phe
        275                 280

<210> SEQ ID NO 2
<211> LENGTH: 840
<212> TYPE: DNA
<213> ORGANISM: Sphingomonas sp. CR-0310201

<400> SEQUENCE: 2
atgagaatag ctctcgcagg cgccggcgca ttcggcgaaa acatctcga cggtctcaag      60 aatatcgacg gcgtcgagat cgtctcgatc atcagccgca aggccgagca ggccgcggaa    120

-continued

```
gtcgccgcga aatatggcgc gaagcacagc ggcaccgatc tttccgaagc gcttgcccgt      180
gacgatgtcg acgcggtgat cctctgcacc cccacccaga tgcatgccga gcaggccatt      240
gcctgcatga atgccggcaa gcatgtccag gtggaaatcc cgctggcgga cagctgggcc      300
gatgccgaag cggtgatgaa gaagagccag gaaaccggcc tcgtctgcat ggtcggccac      360
acccgccgct tcaacccgag ccaccagtat atccacaaca gatcgtggc cggcgagctc      420 gccatccagc agatggacgt gcagacctat ttcttccgcc gcaagaacat gaacgccaag      480
ggcgagccgc ggtcctggac ggaccatctg ctctggcacc atgccgcgca cacggtggac      540
ctgttcgctt atcaggccgg caagatcgtg caggccaatg ccgtgcaggg gccgatccat      600
cccgagctcg gcatcgccat ggacatgtcg atccagctca agagcgagac gggcgcgatc      660
tgcaccctgt ccctctcgtt caacaatgac gggccgctcg gcaccttctt ccgctacatc      720
tgcgacaacg gcacctggat cgcgcgctac gacgatctgg tgaccggcaa ggaagaaccc      780
gtggacgtca gcaaggtcga cgtgtcgatg aacgggatcg agctgcagga tcgggaattc      840
```

<210> SEQ ID NO 3
<211> LENGTH: 315
<212> TYPE: PRT
<213> ORGANISM: Sphingomonas sp. CR-0310201

<400> SEQUENCE: 3

```
Met Arg Ile Ala Leu Ala Gly Ala Gly Ala Phe Gly Glu Lys His Leu
 1               5                  10                  15

Asp Gly Leu Lys Asn Ile Asp Gly Val Glu Ile Val Ser Ile Ile Ser
            20                  25                  30

Arg Lys Ala Glu Gln Ala Ala Glu Val Ala Ala Lys Tyr Gly Ala Lys
        35                  40                  45

His Ser Gly Thr Asp Leu Ser Glu Ala Leu Ala Arg Asp Asp Val Asp
    50                  55                  60

Ala Val Ile Leu Cys Thr Pro Thr Gln Met His Ala Glu Gln Ala Ile
65                  70                  75                  80

Ala Cys Met Asn Ala Gly Lys His Val Gln Val Glu Ile Pro Leu Ala
                85                  90                  95

Asp Ser Trp Ala Asp Ala Glu Ala Val Met Lys Lys Ser Gln Glu Thr
            100                 105                 110

Gly Leu Val Cys Met Val Gly His Thr Arg Arg Phe Asn Pro Ser His
        115                 120                 125

Gln Tyr Ile His Asn Lys Ile Val Ala Gly Glu Leu Ala Ile Gln Gln
    130                 135                 140

Met Asp Val Gln Thr Tyr Phe Arg Arg Lys Asn Met Asn Ala Lys
145                 150                 155                 160

Gly Glu Pro Arg Ser Trp Thr Asp His Leu Leu Trp His His Ala Ala
                165                 170                 175

His Thr Val Asp Leu Phe Ala Tyr Gln Ala Gly Lys Ile Val Gln Ala
            180                 185                 190

Asn Ala Val Gln Gly Pro Ile His Pro Glu Leu Gly Ile Ala Met Asp
        195                 200                 205

Met Ser Ile Gln Leu Lys Ser Glu Thr Gly Ala Ile Cys Thr Leu Ser
    210                 215                 220

Leu Ser Phe Asn Asn Asp Gly Pro Leu Gly Thr Phe Phe Arg Tyr Ile
225                 230                 235                 240

Cys Asp Asn Gly Thr Trp Ile Ala Arg Tyr Asp Asp Leu Val Thr Gly
                245                 250                 255
```

```
Lys Glu Glu Pro Val Asp Val Ser Lys Val Asp Val Ser Met Asn Gly
            260                 265                 270

Ile Glu Leu Gln Asp Arg Glu Phe Ile Ala Ala Ile Arg Glu Gly Arg
        275                 280                 285

Glu Pro Asn Ser Ser Val Ala Arg Val Leu Asp Cys Tyr Arg Val Leu
    290                 295                 300

Gly Glu Leu Glu Val Gln Leu Glu Lys Gln Gly
305                 310                 315

<210> SEQ ID NO 4
<211> LENGTH: 945
<212> TYPE: DNA
<213> ORGANISM: Sphingomonas sp. CR-0310201

<400> SEQUENCE: 4
atgagaatag ctctcgcagg cgccggcgca ttcggcgaaa acatctcga cggtctcaag      60 aatatcgacg gcgtcgagat cgtctcgatc atcagccgca aggccgagca ggccgcggaa    120
gtcgccgcga aatatggcgc gaagcacagc ggcaccgatc tttccgaagc gcttgcccgt    180
gacgatgtcg acgcggtgat cctctgcacc cccacccaga tgcatgccga gcaggccatt    240
gcctgcatga atgccggcaa gcatgtccag gtggaaatcc cgctggcgga cagctgggcc    300
gatgccgaag cggtgatgaa aagagccag gaaaccggcc tcgtctgcat ggtcggccac    360
acccgccgct tcaaccccag ccaccagtat atccacaaca gatcgtggc cggcgagctc    420 gccatccagc agatggacgt gcagacctat ttcttccgcc gcaagaacat gaacgccaag    480
ggcgagccgc ggtcctggac ggaccatctg ctctggcacc atgccgcgca cacggtggac    540
ctgttcgctt atcaggccgg caagatcgtg caggccaatg ccgtgcaggg gccgatccat    600
cccgagctcg gcatcgccat ggacatgtcg atccagctca agagcgagac gggcgcgatc    660
tgcaccctgt ccctctcgtt caacaatgac gggccgctcg gcaccttctt ccgctacatc    720
tgcgacaacg gcacctggat cgcgcgctac gacgatctgg tgaccggcaa ggaagaaccc    780
gtggacgtca gcaaggtcga cgtgtcgatg aacgggatcg agctgcagga tcgggaattc    840
atcgcggcga tccgcgaagg tcgcgagccc aattcgtcgg tggcgagagt gctcgattgc    900
tatcgggtgc tgggcgaact cgaggtccag ctcgaaaagc agggc                    945

<210> SEQ ID NO 5
<211> LENGTH: 1174
<212> TYPE: DNA
<213> ORGANISM: Sphingomonas sp. CR-0310201
<220> FEATURE:
<221> NAME/KEY: CDS
<222> LOCATION: (129)..(1073)

<400> SEQUENCE: 5
ctcgagggga gagggttggg agaggggtcg ccacgctgcg gcgtgtcagc ccgctcctct     60 cctcccgcc cccttcccg gccctctccc tcgcaggtga gagggcgctc atgtgaaagg      120 actgcccc atg aga ata gct ctc gca ggc gcc ggc gca ttc ggc gaa aaa    170
         Met Arg Ile Ala Leu Ala Gly Ala Gly Ala Phe Gly Glu Lys
              1               5                   10 cat ctc gac ggt ctc aag aat atc gac ggc gtc gag atc gtc tcg atc    218
His Leu Asp Gly Leu Lys Asn Ile Asp Gly Val Glu Ile Val Ser Ile
 15                  20                  25                  30 atc agc cgc aag gcc gag cag gcc gcg gaa gtc gcc gcg aaa tat ggc    266
Ile Ser Arg Lys Ala Glu Gln Ala Ala Glu Val Ala Ala Lys Tyr Gly
                 35                  40                  45
```

```
gcg aag cac agc ggc acc gat ctt tcc gaa gcg ctt gcc cgt gac gat       314
Ala Lys His Ser Gly Thr Asp Leu Ser Glu Ala Leu Ala Arg Asp Asp
             50                  55                  60 gtc gac gcg gtg atc ctc tgc acc ccc acc cag atg cat gcc gag cag       362
Val Asp Ala Val Ile Leu Cys Thr Pro Thr Gln Met His Ala Glu Gln
         65                  70                  75 gcc att gcc tgc atg aat gcc ggc aag cat gtc cag gtg gaa atc ccg       410
Ala Ile Ala Cys Met Asn Ala Gly Lys His Val Gln Val Glu Ile Pro
     80                  85                  90 ctg gcg gac agc tgg gcc gat gcc gaa gcg gtg atg aag aag agc cag       458
Leu Ala Asp Ser Trp Ala Asp Ala Glu Ala Val Met Lys Lys Ser Gln
 95                 100                 105                 110 gaa acc ggc ctc gtc tgc atg gtc ggc cac acc cgc cgc ttc aac ccg       506
Glu Thr Gly Leu Val Cys Met Val Gly His Thr Arg Arg Phe Asn Pro
                115                 120                 125 agc cac cag tat atc cac aac aag atc gtg gcc ggc gag ctc gcc atc       554
Ser His Gln Tyr Ile His Asn Lys Ile Val Ala Gly Glu Leu Ala Ile
            130                 135                 140 cag cag atg gac gtg cag acc tat ttc ttc cgc cgc aag aac atg aac       602
Gln Gln Met Asp Val Gln Thr Tyr Phe Phe Arg Arg Lys Asn Met Asn
        145                 150                 155 gcc aag ggc gag ccg cgg tcc tgg acg gac cat ctg ctc tgg cac cat       650
Ala Lys Gly Glu Pro Arg Ser Trp Thr Asp His Leu Leu Trp His His
    160                 165                 170 gcc gcg cac acg gtg gac ctg ttc gct tat cag gcc ggc aag atc gtg       698
Ala Ala His Thr Val Asp Leu Phe Ala Tyr Gln Ala Gly Lys Ile Val
175                 180                 185                 190 cag gcc aat gcc gtg cag ggg ccg atc cat ccc gag ctc ggc atc gcc       746
Gln Ala Asn Ala Val Gln Gly Pro Ile His Pro Glu Leu Gly Ile Ala
                195                 200                 205 atg gac atg tcg atc cag ctc aag agc gag acg ggc gcg atc tgc acc       794
Met Asp Met Ser Ile Gln Leu Lys Ser Glu Thr Gly Ala Ile Cys Thr
            210                 215                 220 ctg tcc ctc tcg ttc aac aat gac ggg ccg ctc ggc acc ttc ttc cgc       842
Leu Ser Leu Ser Phe Asn Asn Asp Gly Pro Leu Gly Thr Phe Phe Arg
        225                 230                 235 tac atc tgc gac aac ggc acc tgg atc gcg cgc tac gac gat ctg gtg       890
Tyr Ile Cys Asp Asn Gly Thr Trp Ile Ala Arg Tyr Asp Asp Leu Val
    240                 245                 250 acc ggc aag gaa gaa ccc gtg gac gtc agc aag gtc gac gtg tcg atg       938
Thr Gly Lys Glu Glu Pro Val Asp Val Ser Lys Val Asp Val Ser Met
255                 260                 265                 270 aac ggg atc gag ctg cag gat cgg gaa ttc atc gcg gcg atc cgc gaa       986
Asn Gly Ile Glu Leu Gln Asp Arg Glu Phe Ile Ala Ala Ile Arg Glu
                275                 280                 285 ggt cgc gag ccc aat tcg tcg gtg gcg aga gtg ctc gat tgc tat cgg      1034
Gly Arg Glu Pro Asn Ser Ser Val Ala Arg Val Leu Asp Cys Tyr Arg
            290                 295                 300 gtg ctg ggc gaa ctc gag gtc cag ctc gaa aag cag ggc tgaaaacctg      1083
Val Leu Gly Glu Leu Glu Val Gln Leu Glu Lys Gln Gly
        305                 310                 315 caccggaatg aaacggaagc cttgccggag caatctggca aggcttttttt cttggcggca   1143 ggcacgccgt cattgcatca tggcggtgga a                                   1174
```

<210> SEQ ID NO 6
<211> LENGTH: 315
<212> TYPE: PRT
<213> ORGANISM: Sphingomonas sp. CR-0310201

```
<400> SEQUENCE: 6

Met Arg Ile Ala Leu Ala Gly Ala Gly Ala Phe Gly Glu Lys His Leu
 1               5                  10                  15

Asp Gly Leu Lys Asn Ile Asp Gly Val Glu Ile Val Ser Ile Ile Ser
                20                  25                  30

Arg Lys Ala Glu Gln Ala Ala Glu Val Ala Ala Lys Tyr Gly Ala Lys
            35                  40                  45

His Ser Gly Thr Asp Leu Ser Glu Ala Leu Ala Arg Asp Asp Val Asp
        50                  55                  60

Ala Val Ile Leu Cys Thr Pro Thr Gln Met His Ala Glu Gln Ala Ile
65                  70                  75                  80

Ala Cys Met Asn Ala Gly Lys His Val Gln Val Glu Ile Pro Leu Ala
                85                  90                  95

Asp Ser Trp Ala Asp Ala Glu Ala Val Met Lys Lys Ser Gln Glu Thr
                100                 105                 110

Gly Leu Val Cys Met Val Gly His Thr Arg Arg Phe Asn Pro Ser His
            115                 120                 125

Gln Tyr Ile His Asn Lys Ile Val Ala Gly Leu Ala Ile Gln Gln
        130                 135                 140

Met Asp Val Gln Thr Tyr Phe Arg Arg Lys Asn Met Asn Ala Lys
145                 150                 155                 160

Gly Glu Pro Arg Ser Trp Thr Asp His Leu Leu Trp His His Ala Ala
                165                 170                 175

His Thr Val Asp Leu Phe Ala Tyr Gln Ala Gly Lys Ile Val Gln Ala
                180                 185                 190

Asn Ala Val Gln Gly Pro Ile His Pro Glu Leu Gly Ile Ala Met Asp
            195                 200                 205

Met Ser Ile Gln Leu Lys Ser Glu Thr Gly Ala Ile Cys Thr Leu Ser
210                 215                 220

Leu Ser Phe Asn Asn Asp Gly Pro Leu Gly Thr Phe Phe Arg Tyr Ile
225                 230                 235                 240

Cys Asp Asn Gly Thr Trp Ile Ala Arg Tyr Asp Asp Leu Val Thr Gly
                245                 250                 255

Lys Glu Glu Pro Val Asp Val Ser Lys Val Asp Val Ser Met Asn Gly
                260                 265                 270

Ile Glu Leu Gln Asp Arg Glu Phe Ile Ala Ala Ile Arg Glu Gly Arg
            275                 280                 285

Glu Pro Asn Ser Ser Val Ala Arg Val Leu Asp Cys Tyr Arg Val Leu
        290                 295                 300

Gly Glu Leu Glu Val Gln Leu Glu Lys Gln Gly
305                 310                 315

<210> SEQ ID NO 7
<211> LENGTH: 9
<212> TYPE: PRT
<213> ORGANISM: Sphingomonas sp. CR-0310201

<400> SEQUENCE: 7

Asp Asp Val Asp Ala Val Ile Leu Cys
 1               5

<210> SEQ ID NO 8
<211> LENGTH: 12
<212> TYPE: PRT
<213> ORGANISM: Sphingomonas sp. CR-0310201
```

-continued

```
<400> SEQUENCE: 8

Thr Gly Lys Glu Glu Pro Val Asp Val Ser Lys Val
 1               5                  10

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
acgcggtgat cctctgc                                                   17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10
cttgctgacg tccacgg                                                   17
```